(12) United States Patent
Garvin

(10) Patent No.: US 11,781,127 B2
(45) Date of Patent: Oct. 10, 2023

(54) HOMOGENEOUS METHOD TO PREPARE SPERM DNA FROM SEXUAL ASSAULT CASES

(76) Inventor: Alex Garvin, Durmenach (FR)

( * ) Notice: Subject to any disclaimer, the term of this patent is extended or adjusted under 35 U.S.C. 154(b) by 0 days.

(21) Appl. No.: 12/008,385

(22) Filed: Jan. 11, 2008

(65) Prior Publication Data

US 2008/0261293 A1    Oct. 23, 2008

Related U.S. Application Data

(60) Provisional application No. 60/880,497, filed on Jan. 16, 2007.

(51) Int. Cl.
  *C12N 15/10*  (2006.01)
(52) U.S. Cl.
  CPC .............................. *C12N 15/1003* (2013.01)
(58) Field of Classification Search
  CPC ................................................ C12N 15/1003
  See application file for complete search history.

(56) References Cited

U.S. PATENT DOCUMENTS

| 2003/0215845 | A1* | 11/2003 | Bille | |
| 2004/0038213 | A1* | 2/2004 | Kwon | |
| 2004/0063213 | A1* | 4/2004 | Hirai et al. | 436/87 |
| 2005/0084862 | A1* | 4/2005 | Lee et al. | |

FOREIGN PATENT DOCUMENTS

WO    WO04090114    * 10/2004

OTHER PUBLICATIONS

Bianchi (Biology of Reproduction (1993) vol. 49, 1083-1088.*
Uchiyama et al (Japanese Journal of Forensic Science and Technology (2006) vol. 11, pp. 105-122).*
Yoshida et al (Forensic Science International (1995) vol. 72, pp. 25-33).*
Robinson et al (Biochemistry (1975) vol. 14, pp. 369-378).*
Connolly et al (The Journal of Cell biology (1989) vol. 108, p. 299).*
Webster Ninth New Collegiate dictionary (1985) (p. 185).*
Sigma-Aldrich MSDS (Jul. 18, 2008).*
Burton et al ( In J Petide Protein research (1982) vol. 19, pp. 372-379.*
Yakovlev et al (Molecular biology (2006) vol. 40, pp. 867-874).*
Parkes (J. Med. Chem., 2003, 46 (7), pp. 1153-1164).*
Greenspoon et al (J Forensic Science (2004) vol. 49, pp. 1-11).*
Eshleman ( Electrophoresis 2001, 22, 4316-4319).*
Atkinson (Molecular Reproduction and Development (1991) vol. 29, pp. 1-5).*
Nakanishi and Iritani (Molecular Reproduction and Development (1993) vol. 38, pp. 258-261).*
Gill et al (Nature (1985) vol. 318, pp. 577-579).*
Van Santen (Virology (1991) vol. 65, p. 5211).*
Winkler ( Biochmica et Biorphysica Acta (1998) vol. 1406, pp. 219-227).*
Totorella (Brazialian Journal of Medical and Biological research (1997) vol. 30, pp. 387-393).*
Sanyal et al (Molecular biotechnology (1997) vol. 8, pp. 135-137).*
Garvin (Journal of Forensic Sciences (2009) vol. 54, pp. 1297-1303).*
Eisenberg, Ph.D., Arthur; "Spermatozoa Capture During the Differential Extraction Process for STR Typing of Sexual Assault Evidence;" U.S. Dept. of Justice; National Criminal Justice Reference Service; Agency Grant No. 2000-IJ-CX-K0009; Doc No. 197532; Nov. 2002; pp. 1-5 (includes Grant info on p. 5).
Giusti, Alan, et al.; "Application of Deoxyribonucleic Acid (DNA) Polymorphisms to the Analysis of DNA Recovered from Sperm;" Journal of Forensic Sciences, JFSCA, vol. 31, No. 2, Apr. 1986 pp. 409-417.
Wiegand, P., et al; "DNA Extraction for Mixtures of Body Fluid Using Mild Preferential Lysis;" International Journal of Legal Medicine; (1992) 104;pp. 359-360.
Garvin, Alex M., et al.; "DNA Preparation from Sexual Assault Cases by Selective Degradation of Contaminating DNA from the Victim;" Journal of Forensic Science 2009; doi: 10.11111/j.1556-4029.01180.X; pp. 7; www.interscience.wiley.com.

* cited by examiner

*Primary Examiner* — Steven Pohnert

(57) ABSTRACT

The present invention provides a method for the isolation of sperm DNA from swabs taken from rape victims without having to perform a change in buffers. Non-sperm cells from the victim are digested with an enzyme and solubilized, and then in the same buffer an enzyme capable of digesting soluble DNA is added and the victim's DNA is degraded, leaving only the rapist's DNA intact. Since no change of buffer is needed, no centrifugation or filtration steps are needed. The inventive method has utility particularly in the forensic science field.

6 Claims, 2 Drawing Sheets

HOMOGENEOUS METHOD TO PREPARE SPERM DNA FROM SEXUAL ASSAULT CASES

CROSS-REFERENCE TO RELATED APPLICATIONS

This application claims the benefit of priority, under U.S.C. Section 119(e) to U.S. Provisional Application No. 60/880,497 to Alex M. Garvin, entitled "SELECTIVE DEGRADATION OF DNA FROM A MIXTURE," filed 16 Jan. 2007, the subject matter of which is incorporated in its entirety by reference herein.

FIELD OF THE INVENTION

The present invention relates to isolation of sperm DNA from a mixture of sperm and non-sperm cells. The inventive method has utility in forensic analyses.

BACKGROUND

Police departments in the United States currently have a backlog of as many as 500,000 unprocessed swabs taken from rape victims, and the identity of the rapist can be determined by profiling the sperm DNA present on these swabs. Sperm are normally obtained from a rape victim by rubbing a swab against a mucous membrane, resulting in large numbers of the victim's epithelial cells being collected with the rapist's sperm, and these epithelial cells contain large amounts of the victim's DNA. The victim's DNA acts as a contaminant that must be removed from the sperm prior to purification and analysis of the sperm DNA.

The standard method for purifying sperm from vaginal swabs is to first resuspend all cells from the swab and to selectively digest the victim's epithelial cells with a solution containing Proteinase K and SDS (sodium dodecyl sulfate). Sperm nuclei are impervious to this treatment because they have disulfide bond cross-linked thiol-rich proteins, while other cell types are digested and the corresponding DNA is solubilized. The intact sperm are separated from the solubilized, contaminating DNA by centrifugation, careful removal of supernatant, and extensive washing of the sperm pellet (see e.g., Giusti et al., J Forensic Sci., 31:409-417, 1986; Gill et al. Nature 318:577-579, 1985; Wiegand et al., Int J Legal Med, 104:359-360, 1992; and Yoshida et al., Forensic Sci Int., 72:25-33, 1995). Unfortunately, the processes of centrifugation and careful removal of supernatant are difficult to automate, labor intensive, and result in the loss of some sperm.

Uchiyama et al (Japanese Journal of Forensic Science and Technology Volume 1 1, Number 1, p 105-1 12, 2006) show that the sperm pellet washing steps can be avoided by selectively degrading the victim's DNA with DNAse I following digestion of the epithelial cells with proteinase K/SDS, pelleting of the sperm, and removal of the supernatant, and resuspension of the sperm pellet in a DNAse I buffer (see FIG. 1 of paper). While this group found that DNAse I digests soluble DNA and does not digest the sperm DNA (an essential component of the present invention), they did not attempt to develop a centrifugation-free method, namely they did not consider using a buffer that would allow Proteinase K to digest the epithelial cells AND DNAse I to digest the solubilized DNA. Since DNAse I is not active in SDS, this approach requires a buffer change, which requires centrifugation. All prior art that uses a detergent, including the Uchiyama paper, uses an SDS or Sarkosyl containing buffer for the proteinase K lysis step, and this type of buffer is incompatible with DNAse I digestion of the solubilized DNA, unless the SDS is removed.

Chen et al. (J Forensic Science 43:114-118, 1998) propose to separate the sperm from the epithelial cells before preferential lysis by gravitational or mild vacuum filtration through a 5-10 micron nylon mesh membrane which is supposed to retain the epithelial cells while the sperm pass through. DNA is then prepared from the sperm collected in the filtrate. Unfortunately the pores of these filters will expand under pressure requiring that only gravity be used as the driving force to minimize the unwanted passage of epithelial cells. In the absence of a strong driving force, capillary action on the filter surface competes with gravity flow through the filter and results in a large retention volume and difficulties with sample handling (present applicant's observation). Furthermore, DNA from epithelial cells lysed by the harsh detergent required for efficient cell re-suspension will pass through the filter with intact sperm.

Garvin (J Forensic Science 48:1084-7, 2003) and Bille (US patent application 20030215845) showed that sperm could be separated from digested epithelial cell DNA by collecting the sperm on a filter while allowing the solubilized DNA to pass through the filter. Although this method avoids centrifugation, it still requires a separation step, and the sperm DNA must be eluted from the filter, a process that can result in sperm DNA loss.

Attempts have also been made to use anti-sperm antibody coated magnetic beads (Eisenberg, A. J. "Development of a Spermatozoa Capture System for the Differential Extraction of Sexual Assault Evidence"; paper presented at: Profiling PCR and Beyond Conference, 2002; Washington, D.C.). Epitope stability, however, is a likely problem with this approach when applied to casework, because detergents are required to efficiently elute sperm from the swabs and these detergents destroy most of the epitopes recognized by the anti-sperm antibodies. Magnetic beads have been successfully used for many cell separation applications (Haukanes & Kvam, Biotechnology (N Y). 11:60-63, 1993), but it remains to be seen if they can be used to separate human cells that have been dried onto an adsorbent substrate and then resuspended.

A number of attempts have been made to circumvent the selective lysis process. For example, Y chromosome polymorphic markers can be amplified from unfractionated swab DNA (Sibille, et al., Forensic Sci Int. 125:212-216, 2002). However the data provided cannot be used to probe the autosomal STR profiles in the FBI CODIS database, it won't work when the rape victim is male, and males of the same paternal lineage usually have identical Y chromosome STR patterns.

Another approach towards avoiding selective lysis is to physically separate sperm from intact epithelial cells. This has been done by flow cytometry (Schoell et al., Obstet Gynecol. 94:623-627, 1999), however this technique is inherently slow due to the need to analyze and sort one cell at a time and is unlikely to be applied to casework.

SUMMARY OF THE INVENTION

The present invention provides a method for the isolation of sperm DNA from samples having at least one other cell type. The method is based on selective degradation of non-sperm cells and then, in essentially the same buffer, degradation of the DNA that was contained within these cells by treatment with a DNA degrading agent that selectively degrades non-sperm cell DNA. The inventive method has utility in the forensics field.

Preferred aspects provide an identification method, comprising: obtaining sperm DNA according to the above described methods; and determining an identity for the sperm donor, based on the isolated sperm DNA. Preferably, the identity determined is that of a perpetrator of a sexual assault.

The inventive method is applicable in the forensic setting for high throughput processing of samples, such as swabs from sexual assault victims, to obtain a sperm DNA profile, wherein such swabs contain in addition to a relatively small amount of sperm a much larger amount of the victim's epithelial cells and possibly blood cells.

Therefore, it is an object of the invention to create a method for processing samples containing a mixture of sperm and other cells (in particular epithelial cells or blood cells) with the aim of analyzing the sperm DNA contained in the sample. The preferred method is fast, suitable for automation, and provides reliable results even when the amount of sperm present in a test sample is much smaller than the amount of non-sperm cells.

DETAILED DESCRIPTION OF THE INVENTION

Figure 1:
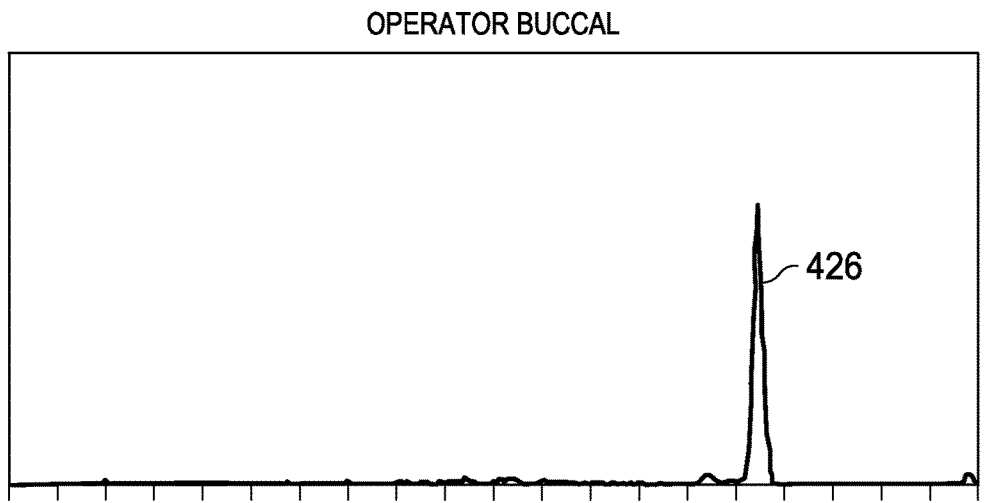
FIG. 1 shows an operator buccal control fraction made from buccal DNA.
Figure 2:
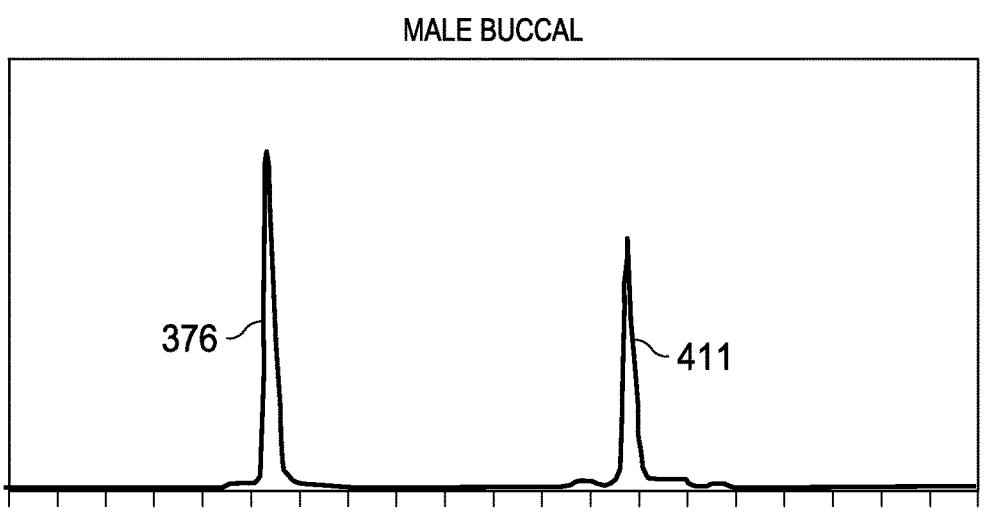
FIG. 2 shows a male buccal control fraction made from male buccal DNA.
Figure 3:
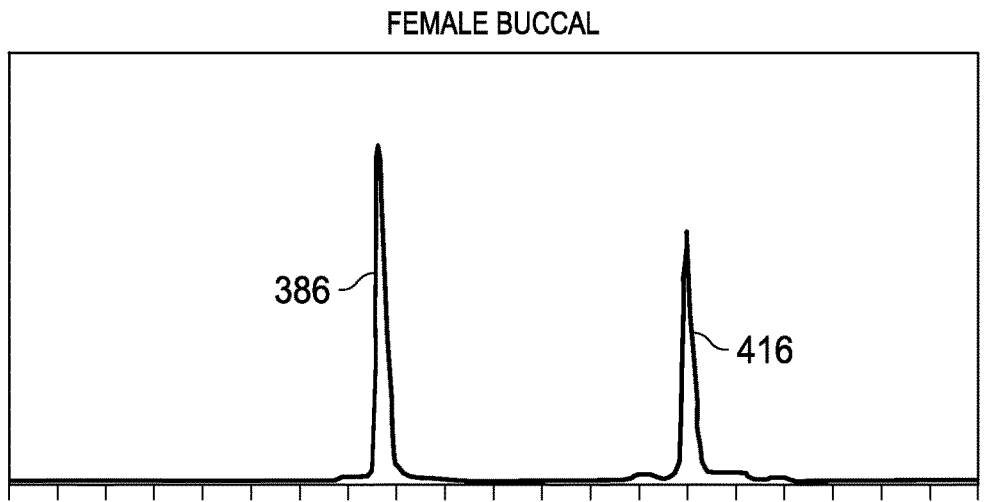
FIG. 3 shows a female buccal control fraction made from female buccal DNA.
Figure 4:
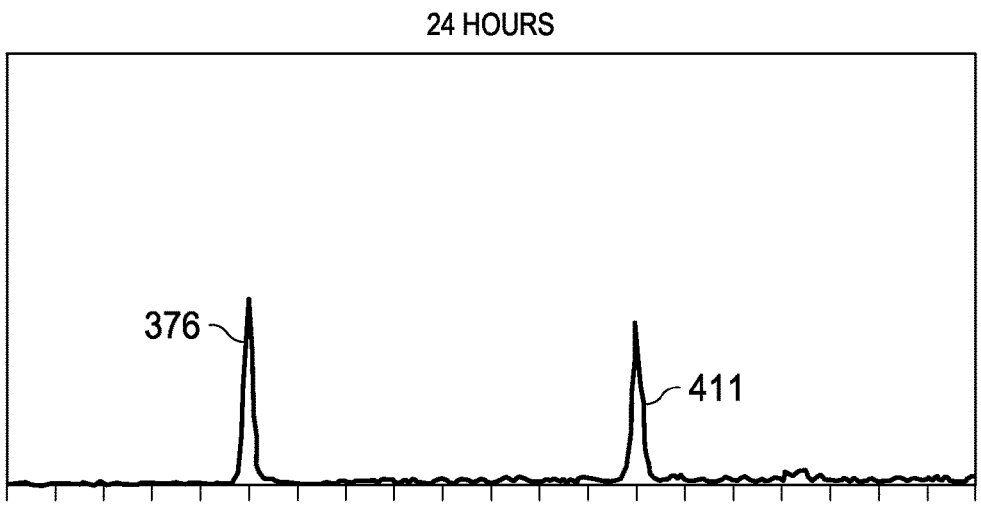
FIG. 4 shows post-coital vaginal swabs taken at twenty four hours after coitus.
Figure 5:
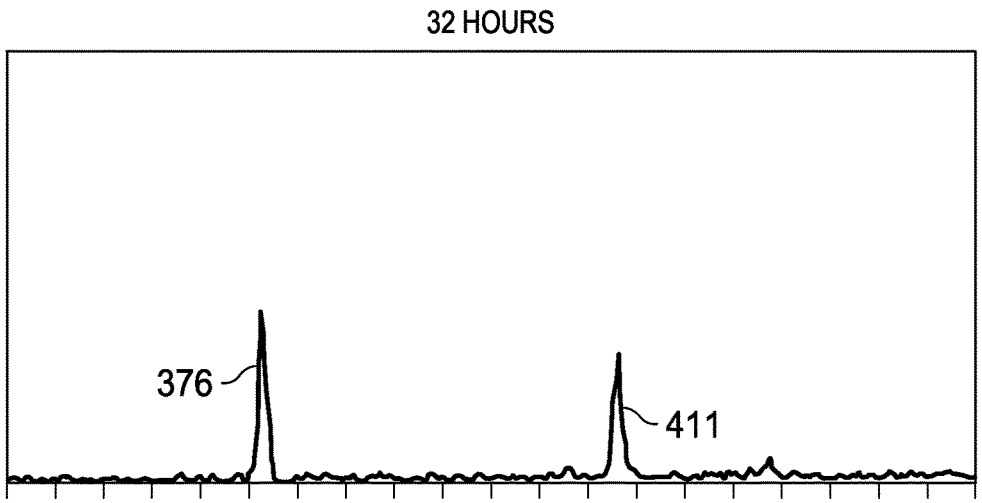
FIG. 5 shows post-coital vaginal swabs taken at thirty two hours after coitus.
Figure 6:
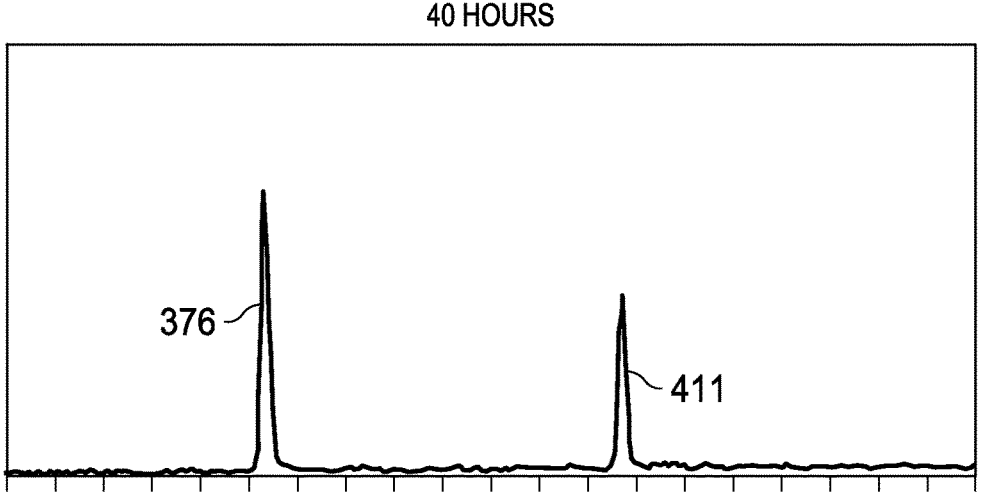
FIG. 6 shows post-coital vaginal swabs taken at forty hours after coitus.

A sample of sperm and non-sperm cells present on a swab must be resuspended before DNA can be isolated. The standard method is to use a 2% SDS/proteinase K solution to do this. The present invention proposes instead to use a high concentration of an effective detergent, plus proteinase K, to do the same thing, however, the detergent must be compatible with downstream processes, namely digestion of soluble DNA with DNAse I. Therefore a different detergent must be used. Triton X-100 at 2% concentration is an effective detergent that can solubilize proteins and DNA, yet DNAse I is active in Triton X-100 at 2%, while it is not active in 2% SDS. Triton X-100 is t-octylphenoxypolyethoxyethanol. The first step is to resuspend the cells from the swab cutting in a 500 ul solution containing: 2% Triton X-100, 20 mM Tris pH 8.0, and proteinase K at 400 µg/ml. Tris pH 8.0 is to insure that the buffer is not at an acidic pH (which will degrade DNA) and Proteinase K is required to digest the non-sperm cells. The swab cutting in vortexed 10 seconds and then incubated in this buffer for 2 hours at 56 degrees. A 10% aliquot (50 µl) of the solution is removed to obtain the victim's DNA fraction.

The next step is to degrade the solubilized non-sperm DNA without having to change the buffer. This is done by transferring 350 µl of the Proteinase K digested material to a fresh tube (the swab cutting is left behind) and adding: 6 mM $CaCl_2$, 6 mM $MgCl_2$, and 360 units of DNAse I. The calcium and magnesium are added to activate the DNAse I enzyme. The DNAse I is allowed to digest soluble DNA by incubation at 56 degrees for 1 hour. Importantly, the DNAse I is active in the buffer that it is placed in, which would not be the case if SDS were in the buffer.

The next step is to inactivate the nuclease, and to lyse the sperm. This is done by adding: 25 mM EDTA (ethylene diamine tetra acidic acid), and 50 mM DTT (dithiothreitol). Incubation is for 5 minutes at 56 degrees.

The sperm DNA is now in solution and free of non-sperm DNA, and ready for further purification. The DNA is in a buffer that is compatible with many down-stream purification methods, such as guanidinium/magnetic silica beads and charge/Switch magnetic beads.

EXAMPLES 50,000 sperm were treated using the above protocol, either with or without DNAse I treatment. DNA was isolated using Qiagen microamp columns, and resuspended in 20 µl of AE buffer. The DNA was quantified using a qPCR assay capable of detecting sub-picogram amounts of DNA. The qPCR assay uses a SyberGreen dye and primers to amplify the 18s ribosome genes. The results are as follows:

No DNase: 42 nanograms
Plus DNase: 39 nanograms

These results show that DNAse I treatment does no degrade sperm DNA.

Epithelial cells from a buccal swab were then digested with 1 ml 2% Triton X-100, 20 mM Tris pH 8.0, and proteinase K at 400 µg/ml for 4 hours at 56 degrees, and this solution was split in half. Half was treated with DNAse I as described above and half was not treated with DNAse I. The DNA was isolated using Qiagen microamp columns, resuspended in 20 µl of AE buffer, and quantitated by qPCR. The results are as follows:

No DNase: 340 nanograms
Plus DNase 300 picograms

Therefore DNase_I treatment can reduce the amount of epithelial cell DNA by over 1000 fold.

Post-coital vaginal swabs were treated with the nuclease protocol and profiled using the PowerPlex 16 kit from Promega. As shown in FIG. 1b, the male fraction DNA obtained from swabs taken at 24, 32, and 40 hours give a clear male profile for the Penta E locus.

The invention claimed is:

1. A method of separating human sperm DNA from human non-sperm DNA in sexual assault samples comprising:
    contacting a sample containing human sperm cells and human non-sperm cells with proteinase-K in an extraction buffer solution comprising t-octylphenoxypolyethoxyethanol, wherein the extraction buffer solution does not contain sodium dodecyl sulfate;
    digesting the human non-sperm cells with the proteinase-K;
    adding a DNAse I to the same extraction buffer solution in which the non-sperm cells were digested without a centrifugation step or a filtration step with respect to the addition of the DNAse I;
    selectively degrading non-sperm DNA from the non-sperm cells with the DNAse I;
    incubating the DNAse I and lysing the sperm by adding ethylenediaminetetraacetic (EDTA) and dithiothreitol (DTT) at 56° C. until the DNAse I is inactivated; and
    separating sperm DNA from the human sperm for further analysis of the sperm DNA.

2. The method of claim 1, further comprising the step of obtaining the sample from a victim of sexual assault.

3. A method of separating human sperm DNA from human non-sperm DNA in sexual assault samples comprising:
    contacting a sample containing human sperm cells and human non-sperm cells with proteinase-K in an extraction buffer solution comprising t-octylphenoxypolyethoxyethanol, wherein the extraction buffer solution does not contain sodium dodecyl sulfate;
    digesting the human non-sperm cells with the proteinase-K;
    adding a DNAse I to the same extraction buffer solution in which the non-sperm cells were digested without a centrifugation step or a filtration step with respect to the addition of the DNAse I;
    selectively degrading non-sperm DNA from the non-sperm cells with the DNAse I;
    inactivating the DNAse I and lysing the sperm by adding ethylenediaminetetraacetic (EDTA) and dithiothreitol (DTT) at 56° C. until the DNAse I is inactivated and the sperm cells are lysed; and
    separating sperm DNA from the human sperm for further analysis of the sperm DNA.

4. The method of claim 3, wherein the sample is obtained from a victim of sexual assault.

5. A method of separating human sperm DNA from human non-sperm DNA in sexual assault samples comprising:
    contacting a sample containing human sperm cells and human non-sperm cells with proteinase-K in an extraction buffer solution comprising t-octylphenoxypolyethoxyethanol, wherein the extraction buffer solution does not contain sodium dodecyl sulfate;
    digesting the human non-sperm cells with the proteinase-K;
    adding a DNAse I to the same extraction buffer solution in which the non-sperm cells were digested without a centrifugation step or a filtration step with respect to the addition of the DNAse I;
    selectively degrading non-sperm DNA from the non-sperm cells with the DNAse I;
    inactivating the DNAse I and lysing the sperm by adding ethylenediaminetetraacetic (EDTA) and dithiothreitol (DTT) for 5 minutes at 56° C.; and
    separating sperm DNA from the human sperm for further analysis of the sperm DNA.

6. The method of claim 5, wherein the sample is obtained from a victim of sexual assault.

\* \* \* \* \*

UNITED STATES PATENT AND TRADEMARK OFFICE
CERTIFICATE OF CORRECTION

| | |
|---|---|
| PATENT NO. | : 11,781,127 B2 |
| APPLICATION NO. | : 12/008385 |
| DATED | : October 10, 2023 |
| INVENTOR(S) | : Alex Garvin |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 784 days.

Signed and Sealed this
Twelfth Day of November, 2024

Katherine Kelly Vidal
*Director of the United States Patent and Trademark Office*